United States Patent [19]

Noguchi et al.

[11] Patent Number: 4,772,331
[45] Date of Patent: Sep. 20, 1988

[54] FLAKY COLORED PIGMENTS, METHODS FOR THEIR PRODUCTION, AND THEIR USE IN COSMETIC COMPOSITIONS

[75] Inventors: Tamio Noguchi, Iwaki; Takaji Watanabe, Ohmiya, both of Japan

[73] Assignee: Merck Patent Gesellschaft Mit Beschrankter Haftung, Darmstadt, Fed. Rep. of Germany

[21] Appl. No.: 922,901

[22] Filed: Oct. 24, 1986

[30] Foreign Application Priority Data

Oct. 25, 1985 [JP] Japan ............................... 60-237779
Oct. 25, 1985 [JP] Japan ............................... 60-237780

[51] Int. Cl.$^4$ .......................... C04B 14/20; C08J 7/04; C09C 3/10; A61K 7/035
[52] U.S. Cl. .................................... 106/417; 106/416; 106/415; 106/479; 514/844; 424/63; 424/69; 424/80; 424/81; 424/83
[58] Field of Search ............... 106/288 B, 291, 308 R, 106/ 308 Q, 901; 514/769, 770, 785, 844, 845, 951; 424/63, 69, 80, 81, 83

[56] References Cited

U.S. PATENT DOCUMENTS

| | | | |
|---|---|---|---|
| 3,914,405 | 10/1975 | Shepherd et al. | 424/49 |
| 3,978,207 | 8/1976 | Fotui et al. | 424/63 |
| 4,108,185 | 8/1978 | Boulogne et al. | 424/63 X |
| 4,325,741 | 4/1982 | Otoi et al. | 424/63 X |
| 4,332,763 | 6/1982 | Hempil et al. | 424/63 X |
| 4,457,784 | 7/1984 | Bernhard | 424/63 X |
| 4,534,963 | 8/1985 | Gordon | 424/63 X |
| 4,591,502 | 5/1986 | Schlossman | 424/63 |
| 4,609,545 | 9/1986 | Schlossman | 424/63 |
| 4,648,908 | 3/1987 | Takasuka et al. | 424/69 X |
| 4,650,672 | 3/1987 | Yagita | 514/844 |

*Primary Examiner*—John F. Terapane
*Assistant Examiner*—Catherine S. Kilby
*Attorney, Agent, or Firm*—Millen & White

[57] ABSTRACT

Colored flaky colored pigments are obtained by uniformly adhering a finely divided color pigment onto a flaky substrate by the use of an high molecular weight organic compound as a binder.

20 Claims, No Drawings

FLAKY COLORED PIGMENTS, METHODS FOR THEIR PRODUCTION, AND THEIR USE IN COSMETIC COMPOSITIONS

BACKGROUND OF THE INVENTION

This invention relates to colored flaky pigments wherein the surface of a flaky substrate is covered with a finely divided color pigment.

It is known that color pigments during the course of their production consist of extremely fine particles which are called primary particles. These particles posses a very high surface energy, and therefore are present in an unstable state and tend to cohere to coarser pigment particles. When a pigment of this nature is used, therefore, the cohering coarse pigment particles are mechanically crushed into primary particles for the purpose of enhancing the color-generating property. The surfaces of the crushed pigment particles also are chemically treated to enable the individual particles of the pigment to be kept in a stably dispersed state. The resultant pigment is easily wetted and dispersed in use. When the pigment treated as described above is left standing for a long time in a vehicle, however, the pigment particles in the vehicle cohere again, possibly to the extent of adversely affecting the color generating property of the pigment.

SUMMARY OF THE INVENTION

It is an object of this invention to provide colored flaky pigments and processes for producing them whereby the primary particles of a color pigment can be deposited on the surface of a flaky substrate, whereby they adhere quickly in a state free from cohesion, thus producing flaky pigments which exhibit satisfactory spreading properties and adhering properties when applied to the skin and which exhibit high coloring properties, especially very good color saturation and which posses transparency resistance to weather conditions, heat and solvents.

Upon further study of the specification and appended claims, further objects and advantages of this invention will become apparent to those skilled in the art.

In a composition aspect, these objects have been attained by providing a colored flaky pigment comprising a flaky substrate, said substrate having a finely divided color pigment material adhered thereto, said pigment material being adhered to said substrate by a binder comprising a high molecular weight organic compound.

In a method aspect, these objects have been attained by providing a process for the production of a colored flaky pigment comprising the step of admixing (A) a suspension or solution of a color pigment and a high molecular weight organic compound in water and/or an alcohol with (B) a suspension of a flaky substrate in a solution of a high molecular weight organic compound in water and/or alcohol.

The invention further concerns the use of these flaky colored pigments in cosmetic compositions.

DETAILED DISCUSSION

Examples of flaky substrates which can be employed in this invention include talc, kaolin and bismuth oxychloride as well as various species of mica such as common mica and sericite which have been used as raw materials for face powder and other similar cosmetic articles. Synnythetic pearl or pearlescent pigments obtained by coating mica with iron oxide or titanium dioxide can also be used. In general, these substrates are used in the form of particles having a width and length of about 1-30, preferably about 4-25 $\mu$m, and having a thickness of about 0.1-1 $\mu$m.

As used herein "color pigment" refers to the coloring agent or material, e.g. the primary particles discussed above. "Flaky pigment" and "colored flaky pigment" refer to compositions of this invention comprising the flaky substrate, the binder and the color pigment.

Examples of high molecular weight organic compounds suitable for use in adhering the color pigment to the flaky substrate include polyethylene glycols, polypropylene glycols, polyvinyl pyrrolidones, polyvinyl alcohols, polyacrylates, polyethylenes, celluloses and derivatives thereof which are generally acceptable for use as raw materials for cosmetic compositions.

In general compounds having molecular weights of from about 500 to about 160,000 can be used. Those having molecular weights of from about 3,000 to about 50,000 are preferred.

In general, acceptable high molecular weight organic compounds include those having sufficient binding properties to effectively adhere the color pigment to the flaky substrate without substantially affecting its colorant properties. These binders are used generally in an amount of from about 0.1 to about 10% by weight, preferably from about 1 to about 7% by weight of the final colored flaky pigment. With respect to the color pigment, the amount of binder is 0.5 to 20 wt. %.

In general, the process for coating the color pigment onto the flaky substrate includes the following steps:

(1) The color pigment can be dispersed in a finely divided state with the aid of, for instance, a sand mill, ball mill or a roll mill in a solution of an organic high molecular weight compound in hot water and/or alcohol. Alternatively, the color pigment is dissolved in a suitable solvent and admixed with a solution of a high molecular weight organic compound in water and/or alcohol.

(2) The flaky substrate is suspended in a solution of a high molecular weight organic compound in water and/or an alcohol.

(3) The suspension or solution of (1) is admixed with the suspension of (2) under conditions causing the organic high molecular weight compound and the color pigment to be precipitated onto the flaky substrate. the precipitated solid is then separated from the suspension and dried.

The resulting colored flaky pigment may be separated by fully conventional means, e.g., vacuum filtration, centrifugation, etc.

The above process provides a colored flaky pigment wherein the pigment color is firmly adhered to the flaky substrate.

Suitable solvents for the organic high molecular weight compound include water and alcohols, especially ethanol, and mixtures thereof. If water is used as the solvent, preferably used as the high molecular weight organic compound is polyethylene glycol with a molecular weight of from about 1,000 to about 10,000 polypropylene glycol with a molecular weight of about 1,000 to about 6,000, or polyvinyl pyrrolidone with a molecular weight of about 10,000 to about 40,000.

According to the present invention organic as well as inorganic color pigments can be deposited onto flaky substrates.

When inorganic pigments, e.g, iron blue, ultramarine blue, iron oxide type pigments, titanium dioxide, zinc oxide, chromium oxide, cobalt blue and cobalt green, are coated onto the flaky substrate, a suspension of the color pigment in the solution of the organic high molecular weight compound is formed in step (1) above.

Organic pigments, however, in general are basic compounds containing azo type and hydrazone type groups as coloring groups in their molecular structures and therefore are capable of forming salts with an acidic substance.

For example, copper phthalocyanine reacts with sulfuric acid and consequently forms a salt. This sulfate is soluble in concentrated sulfuric acid. When the concentration of sulfuric acid is on the order of only 80–65% however, the sulfate is not dissolved but is kept in the form of a slurry in the sulfuric acid. The phthalocyanine pigment in the aforementioned form of an acid paste produces finely divided pigment particles when it is poured into a large volume of water. Hence this pigment can be employed in this slurry form in step (1) above.

Other possibilities of obtaining a solution of organic pigments include dissolving the pigment in a solvent containing a Lewis acid or in a polar organic solvent. Examples of solvents useful for dissolving an organic color pigment or dispersing it in the form of a slurry include concentrated sulfuric acid, Lewis acids such as solutions of aluminum chloride and iron chloride in alcohols, and polar organic solvents such as dimethylformamide, dimethylsulfoxide and tetrahydrofuran, the above listing being merely exemplary.

Examples of organic pigments which can be used effectively in this invention include organic pigments of the quinacridone type, condensed azo type and phthalocyanine type, this listing being merely exemplary. For use in cosmetic articles the following pigments also prove desirable:

Red color: No. 3, No. 104, No. 106, No. 202, No. 204, No. 207, No. 213, No. 223, No. 226 and No. 401.
Yellow color: No. 4, No. 5, No. 203, No. 205 and No. 403.
Blue color: No. 202, No. 203, No. 1 and No. 404.
Green color: No. 3 and No. 201.
Orange color: No. 301, No. 203 and No. 205.
Purple color: No. 401

The above listing is merely exemplary.

By the process according to the invention practically any desired amount of color pigment can be adhered to the flaky substrate. It is thus possible to produce flaky pigments with widely differing color effects. In general, amounts of color pigment of about 0.5 to about 30% by weight and preferably of about 1 to about 20% by weight, referring to the total pigment weight, are used.

The resulting pigments are especially useful in cosmetics. The flaky pigments possess a bright color tone, exhibit satisfactory adhering properties and spreading properties with respect to the skin and prevent the organic and inorganic color pigments from directly contacting the skin. Thus, they serve to decrease possible differential sensation which the color pigment may cause on the skin. It has also been found that such compounds as iron blue and ultramarine blue which have poor resistance to heat can be caused to adhere fast to a flaky substrate in accordance with this invention at a temperature not exceeding 200° C.

The other cosmetically acceptable or compatible components employed in cosmetic formulations are well known to those skilled in the art.

The colored flaky pigments of this invention are especially suitable in powdered cosmetic compositions, e.g., powdery facial and eye cosmetic compositions.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degree Celsius and all parts and percentages are by weight; unless otherwise indicated.

EXAMPLE 1

In 143 g of water, 7.2 g of polyethylene glycol having a molecular weight of about 6,000 was dissolved by heating. In the produced solution, 14 ml of ethanol and 71.5 g of ultramarine blue added thereto were finely divided and dispersed with the aid of a sand mill.

The suspension so obtained was added to a solution of 28 ml of ethanol in 576 g of water. Separately, 500 g of mica 1 to 15 $\mu$m in grain size was suspended in a solution produced by adding a solution of 5.7 g of polyethylene glycol in 140 g of water to 2,500 g of water. To this suspension which was kept stirred, the aforementioned suspension of pigment was added at a rate of 3 ml/min. The solid which was educed in the resultant mixture was separated by filtration and was dried at a temperature of 110° to 140° C. Consequently, there was obtained a blue flaky pigment.

EXAMPLE 2

In 200 g of water, 1 g of polyvinyl alcohol was dissolved by heating. In the produced solution, 50 g of ultramarine blue was finely divided and dispersed with the aid of a sand mill.

To the resultant suspension which was kept stirred, a solution of 1.0 g of polyethylene glycol with a molecular weight of about 8,500 in 100 g of water was added.

Separately, a suspension was prepared by adding 400 g of mica 1 to 15 $\mu$m in grain size to a solution of 4 g of polyethylene glycol in 2,000 g of water. To this suspension, the aforementioned suspension of ultramarine blue was added at a rate of 4 to 6 ml/min. The resultant mixture was filtered and the solid consequently separated, in a state not washed with water, was dried at a temperature in the range of 110° to 140° C. Consequently, there was obtained a blue flaky pigment.

EXAMPLE 3

In 50 g of water, 5 g of polyethylene glycol having a molecular weight of about 6,000 was dissolved by heating. In the solution so produced, 10 g of iron blue was finely divided and dispersed with the aid of a sand mill.

To the suspension, a solution prepared by dissolving 3 g of polyethylene glycol in 300 g of water by heating was added.

Separately, 190 g of mica 1 to 15 $\mu$m in grain size was suspended in a solution of 3 g of polyethylene glycol in 1,500 g of water. To the resultant suspension which was kept stirred, the aforementioned suspension of pigment was added at a rate of 3 ml/min. The produced mixture was filtered and the separated solid was dried at a tem-

EXAMPLE 4

A pigment was prepared by following the procedure of Example 1, except that talc was used as a flaky substrate in the place of mica.

EXAMPLE 5

A pigment was prepared by following the procedure of Example 3, except that talc was used as a flaky substrate in the place of mica.

EXAMPLE 6

A pigment was prepared by following the procedure of Example 1, except that red oxide was used as a pigment in the place of ultramarine blue.

EXAMPLE 7

A pigment was prepared by following the procedure of Example 1, except that yellow iron oxice was used as a pigment in the place of ultramarine blue.

EXAMPLE 8

A pigment was prepared by following the procedure of Example 1, except that chromium oxide was used as a pigment in the place of ultramarine blue.

EXAMPLE 9

A pigment was prepared by following the procedure of Example 1, except that a pearl pigment obtained by depositing titanium dioxide on mica was used as a flaky substrate in the place of mica.

EXAMPLE 10

A pigment was prepared by following the procedure of Example 1, except that polyvinyl pyrrolidone with a molecular weight of about 18,000 was used in the place of polyethylene glycol.

Under an electron microscope, each of the pigments obtained in the preceding working examples was found to have fine particles of inorganic pigment deposited fast on a flaky substrate. The flaky pigment covered with an inorganic pigment, when used in cosmetic articles such as cheek rouge and eye shadow, exhibits outstanding spreading property and adhering property to the skin.

EXAMPLE 11

In 52 g of concentrated sulfuric acid, 2.5 g of phthalocyanine blue was dissolved. This solution was gradually added to 500 g of an aqueous 60 wt % sulfuric acid solution to prepare a sulfuric acid slurry of phthalocyanine. In the resultant suspension, 150 g of mica coated with titanium dioxide (about 50 % by weight) was thoroughly mixed. The suspension was intimately mixed with a solution of 10 g of polyethylene glycol with a molecular weight of about 8,500 in 2.5 liters of hot water at 50° to 60° C. and the resultant mixture was kept stirred at the same temperature for 20 minutes. The mixture so produced was left cooling to room temperature, then filtered, and washed with water. The solid so separated was dried at a temperature in the range of 120° to 140° C. Consequently, there was obtained a pigment possessing a blue luster.

EXAMPLE 12

A dispersion having 0.3 g of phthalocyanine blue dispersed in a solution of 3.0 g of anhydrous aluminium chloride in 30 g of ethanol and a suspension having 15 g of mica coated with titanium dioxide (about 50% by weight) suspended in a solution of 3 g of polyethylene glycol in 50 g of ethanol were thoroughly mixed. The resultant mixture was dispersed in a solution of 5 g of polyethylene glycol in 500 ml of hot water and stirred therein for five minutes. The resultant dispersion was left cooling to room temperature, filtered, and washed with water. When the resultant solid was dried at a temperature of 120° to 140° C., there was obtained a pigment possessing a blue luster.

When the pigments obtained in Example 11 and Example 12 were independently mixed in a toluene-water two-phase system and then left standing at rest, they passed into the toluene phase (organic layer). This experiment evinces that the pigments are hydrophobic because of the adhesion of organic pigments to the titanium dioxide mica composite.

Under an electron microscope, the pigment produced as described above was found to have fine particles of organic pigment deposited on the flaky substrate.

EXAMPLE 13

In 20 g of dimethyl formamide, 0.2 g of Helindon Pink was dissolved by heating. The resultant solution was thoroughly mixed with a suspension of 10 g of mica in 50 g of ethanol. The suspension so obtained was stirred in a solution of 4 g of polyethylene glycol with a molecular weight of about 8,500 in 200 g of hot water. The mixture obtained consequently was filtered. The solid separated was washed with water and dried at a temperature of 110° to 140° C. Consequently there was obtained a red flaky pigment.

EXAMPLE 14

In 130 g of water, 3.0 g of polyethylene glycol having a molecular weight of about 6,000 was dissolved by heating. In a sand mill, the solution and 14 ml of ethanol and 25 g of Helidon Pink added thereto were kneaded to effect dispersion of pigment. To the resultant suspension which was kept stirred, a solution of 1.0 g of polyethylene glycol in 189 g of water and 1.5 g of ethanol was added.

Separately, a suspension was prepared by adding 500 g of mica 1 to 15 μm in grain size to a solution of 5.5 g of polyethylene glycol in 2,500 g of water and 80 g of ethanol. To this suspension, the aforementioned suspension of organic pigment was added at a rate of 6 to 7 ml/min. Then, the resultant mixture was filtered and the separated solid, in a state not washed with water, was dried at a temperature of 110° to 140° C. Consequently, there was obtained a red flaky pigment.

EXAMPLE 15

A yellow flaky pigment was obtained by following the procedure of Example 14, except that Hanza Yellow was used in the place of Helindon Pink.

EXAMPLE 16

A blue flaky pigment was obtained by following the procedure of Example 14, except that phthalocyanine blue was used in the place of Helindon Pink.

EXAMPLE 17

A red flaky pigment was obtained by following the procedure of Example 14, except that mica having about 17% by weight of iron oxide deposited thereon was used in the place of mica.

EXAMPLE 18

A yellow flaky pigment was obtained by following the procedure of Example 15, except that mica having about 11% by weight of yellow iron oxide deposited thereon was used in the place of mica.

EXAMPLE 19

A red flaky pigment was obtained by following the procedure of Example 14, except that Red No. 202 was used in the place of Helindon Pink.

EXAMPLE 20

In 60 g of water, 3 g of polyethylene glycol having a molecular weight of about 20,000 was dissolved. In a sand mill, the solution and 5 g of Hanza Yellow were mixed to effect dispersion.

Separately, in a solution of 3 g of polyethylene glycol in 300 ml of water, 100 g of mica 1 to 15 $\mu$m in grain size was suspended. To the suspension which was kept heated at 15° to 50° C. and stirred, the aforementioned suspension of organic pigment was added. The resultant mixture was filtered and the separated solid was dried at 110° to 140° C. Consequently, there was obtained a yellow flaky pigment.

EXAMPLE 21

A yellow flaky pigment was obtained by following the procedure of Example 20, except that talc not more than 20 $\mu$m in grain size was used in the place of mica.

EXAMPLE 22

In 150 g of water, 0.30 g of polyvinyl alcohol (#500 with a molecular weight of about 27,000) and 3.0 g of polyethylene glycol having a molecular weight of 6,000 were dissolved by heating. In a sand mill, the solution and 10 g of Helindon Pink added thereto were mixed to effect dispersion. Separately, a suspension was prepared by adding 200 g of mica 1 to 15 $\mu$m in grain size to a solution o 2.5 g of polyethylene glycol in 1,300 g of water. To the suspension which was kept stirred, the aforementioned dispersion of organic pigment was added.

The solid which educed in the mixture was separated by filtration and dried at 105° to 140° C. Consequently, there was obtained a red flaky pigment.

EXAMPLE 23

A red flaky pigment was obtained by following the procedure of Example 22, except that polyvinyl pyrrolidone was used in the place of polyvinyl alcohol.

Under an electron microscope, each of the pigments obtained in the preceding examples was found to have fine particles of organic pigment deposited fast on a flaky substrate.

The flaky pigment covered with an organic pigment prepared as described above, when used in cosmetic articles such as cheek rouge and eye shadow, exhibits excellent spreading property and adhering property to the skin.

The preceding examples can be repeated with similar success by substituting the generically or specifically described reactants and/or operating condition of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Free-flowing colored flaky pigments comprising flaky substrates having a finely divided color pigment material adhered on the surfaces thereof by a high molecular weight organic binder.

2. Flaky pigments of claim 1 wherein said binder is a high molecular weight organic compound having an average molecular weight of from about 50 to about 160,000.

3. Flaky pigments of claim 2 wherein said binder comprises a high molecular weight organic compound having an average molecular weight of from about 3,000 to about 50,000.

4. Flaky pigments of claim 1 comprising from about 0.5 to about 30% by weight of said color pigment and about 0.1 to about 10% by weight of said binder.

5. Flaky pigments of claim 4 comprising from about 1 to about 20% by weight of said color pigment and about 1 to about 7% by weight of said binder and wherein said flaky substrate is talc, kaolin, bismuth oxychloride, mica or a synthetic pearl pigment.

6. Flaky pigments of claim 1 wherein said binder is a polyethylene glycol.

7. Flaky pigments of claim 1 wherein said binder is a polypropylene glycol.

8. Flaky pigments of claim 1 wherein said binder is a polyvinyl pyrrolidone.

9. Flaky pigments of claim 1 wherein said binder is a polyvinyl alcohol.

10. Flaky pigments of claim 1 wherein said binder is a polyacrylate.

11. Flaky pigments of claim 1 wherein said binder is a polyethylene.

12. Flaky pigments of claim 1 wherein said binder is a cellulose or cellulose derivative.

13. A process for the production of a colored flaky pigment comprising admixing (A) a suspension or solution of a color pigment and a high molecular weight organic compound in water and/or an alcohol with (B) a suspension of a flaky substrate in a solution of a high molecular weight organic compound in water and/or alcohol whereby said color material is precipitated onto the surface of said substrate and bound thereto by said high molecular weight organic compound.

14. A process of claim 13 wherein said high molecular weight organic compound has an average molecular weight of from about 50 to about 160,000.

15. A process of claim 14 wherein said high molecular weight organic compound has an average molecular weight of from about 3,000 to about 50,000.

16. In a powdery cosmetic composition comprising colored flaky pigments and at least one other cosmetically compatible component, the improvement wherein said colored flaky pigments are those of claim 1.

17. In a powdery cosmetic composition comprising colored flaky pigments and at least one other cosmetically compatible component, the improvement wherein said colored flaky pigments are those of claim 2.

18. In a powdery cosmetic composition comprising colored flaky pigments and at least one other cosmetically compatible component, the improvement wherein said colored flaky pigments are those of claim 3.

19. Colored flaky pigment produced by the process of claim 13.

20. Colored flaky pigments of claim 3, wherein said binder is selected from the group consisting of polyethylene and polypropylene glycols, polyvinyl pyrrolidones, polyvinyl alcohols, polyacrylates, polyolefins and celloluse and cellulose derivatives.

* * * * *

UNITED STATES PATENT AND TRADEMARK OFFICE
CERTIFICATE OF CORRECTION

PATENT NO. : 4,772,331
DATED : September 20, 1988
INVENTOR(S) : Noguchi et al

It is certified that error appears in the above-identified patent and that said Letters Patent is hereby corrected as shown below:

Column 8, Claim 2, Line 17:

should read: --average molecular weight of from about 500 to about--

Column 8, Claim 14, Line 57:

should read: --weight of from about 500 to about 160,000.--

Signed and Sealed this

First Day of August, 1989

Attest:

DONALD J. QUIGG

Attesting Officer

Commissioner of Patents and Trademarks